United States Patent [19]
Sheely

[11] 3,944,592
[45] Mar. 16, 1976

[54] METHOD OF PRODUCING UNSATURATED NITRILES
[75] Inventor: Harold R. Sheely, Orleans, Mass.
[73] Assignee: The Badger Company, Inc., Cambridge, Mass.
[22] Filed: Dec. 20, 1973
[21] Appl. No.: 426,900

Related U.S. Application Data
[63] Continuation-in-part of Ser. No. 39,592, May 22, 1970, abandoned.

[52] U.S. Cl.......... 260/465.3; 260/294.9; 260/465 C
[51] Int. Cl.² ........................................ C07C 120/14
[58] Field of Search ...................... 260/465.3, 465 C

[56] References Cited
UNITED STATES PATENTS

| | | | |
|---|---|---|---|
| 3,230,246 | 1/1966 | Callahan et al. | 260/465.3 |
| 3,427,343 | 2/1969 | Callahan et al. | 260/465.3 |
| 3,472,892 | 10/1969 | Callahan et al. | 260/465.3 |
| 3,546,268 | 12/1970 | Ikeda et al. | 260/465.3 |
| 3,578,696 | 5/1971 | Blanck | 260/465.3 |

Primary Examiner—Joseph P. Brust
Attorney, Agent, or Firm—Schiller & Pandiscio

[57] ABSTRACT

A method of producing unsaturated nitriles by reaction of an unsaturated hydrocarbon with ammonia and oxygen in a reactor having a fluidized catalyst bed comprising a regeneration zone and a reaction zone, characterized by introducing between about 3 percent and about 90 percent of the total amount of ammonia supplied to the reaction to the regeneration zone together with oxygen and introducing the remainder of the ammonia to the reaction zone together with the hydrocarbon feed.

14 Claims, 1 Drawing Figure

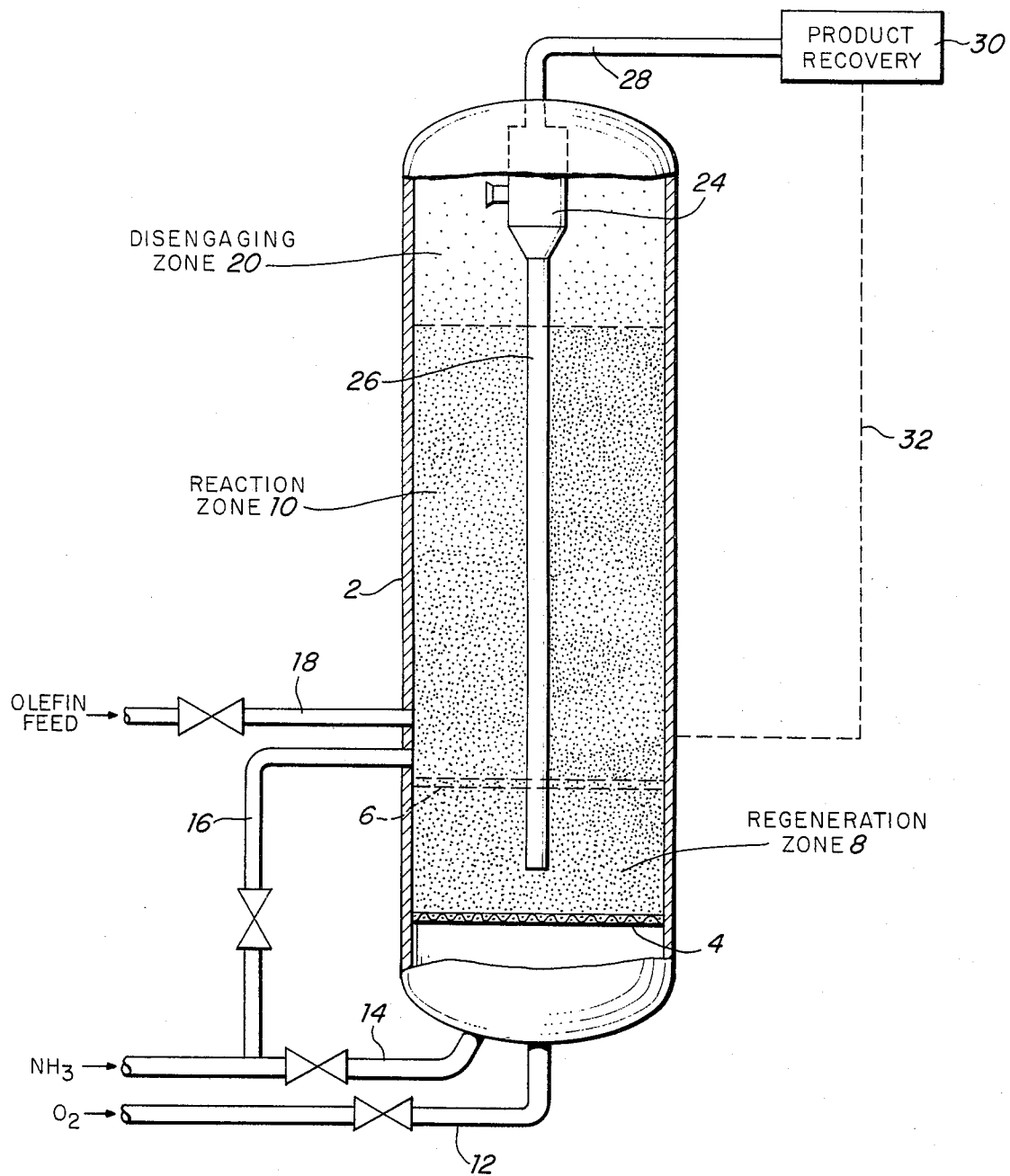

METHOD OF PRODUCING UNSATURATED NITRILES

This is a continuation in part of my copending application Serial No. 39592, filed May 22, 1970 for Method of Producing Unsaturated Nitriles, now abandoned.

This invention relates to the oxidation of unsaturated hydrocarbon-ammonia mixtures to unsaturated nitriles and more particularly to an improvement in the manufacture of an unsaturated nitrile by a process which involves the catalytic vapor phase reaction of oxygen, ammonia, and an unsaturated hydrocarbon in a reactor containing a fluidized catalyst.

Various processes are known in the art for manufacturing unsaturated aliphatic, and aromatic nitriles. For example, U.S. Pat. Nos. 2,499,055, 2,828,325, 2,904,580, 3,005,517, 3,044,966, 3,050,546, 2,197,419, 3,198,750, 3,200,084, 3,248,340, 3,312,710, 3,354,197, 3,365,482, 3,404,947, 3,431,292, 3,433,823, 3,442,771, 3,472,892; British Pat. Nos. 874,593, 904,418, 1,195,037, and 1,246,108; Belgium Pat. Nos. 592,434, 593,097, 598,511, 603,030, 612,136, 615,605, 603,031; Canadian Pat. No. 619,497 and French Pat. No. 1,278,289 teach various processes and catalysts for the ammoxidation of an olefin to produce an unsaturated nitrile. According to these teachings, an olefin such as propylene or isobutylene, a cycloalkene such as cyclohexene, or an alkyl or alkenyl-substituted benzene or naphthalene such as toluene, phenylpropene or methylnaphthalene is reacted with ammonia and molecular oxygen in the vapor phase in the presence of a selected catalyst to produce the corresponding unsaturated nitrile.

Persons skilled in the art are familiar with several modifications in processes of the character described intended to provide improved results and economic savings on a commercial scale. For example, U.S. Pat. No. 3,230,246 suggests that if such process is carried out in a reactor having two or more serially connected catalytic reaction chambers or zones in which the gases being contacted experience very short contact times, the operating results are superior to those obtained under the same reaction conditions in a conventional reactor having a single compartment or reaction zone with the same volume as the total combined volumes of the serially connected compartments or zones. However, even with a reactor having several serially connected catalytic reaction zones, the activity of the catalyst tends to decline in a relatively short period of time, necessitating periodic interruption of the process to permit catalyst regeneration, e.g., by contacting the catalyst with air at an elevated temperature.

With respect to solving this latter problem, U.S. Pat. No. 3,427,343 discloses a further modification which requires that the oxygen always contact the catalyst in the substantial absence of olefin and ammonia. The oxygen is introduced in the first of several serially connected reaction zones, and the other reactants are introduced into a reaction zone that is downstream from the zone to which the oxygen is initially fed. Although the correct explanation for the superior results obtained by the separate introduction of oxygen is not known, the compartment or reaction zone into which the oxygen is introduced is referred as the "catalyst regeneration zone" to signify that the catalyst is regenerated or restored to a previous high valence oxidation state as the result or contact thereof by molecular oxygen in the absence of olefin and ammonia. This modification has been found to maintain the catalyst activity at a uniformly high level, with the result that the process may be carried out continuously for a long time without any substantial drop in percent conversion of feed or yield of desired product. However, with this modification a substantial proportion of the olefin feed is lost by oxidation to carbon monoxide and carbon dioxide.

Accordingly, the essential and primary object of the present invention is to improve on prior art processes such as those described in the above mentioned patents by providing a further modification which significantly reduces the amount of unsaturated hydrocarbon feed lost by oxidation to $CO$ and $CO_2$ and the need for serial reaction zones.

In its broadest sense, the invention is an improved method of producing an unsaturated nitrile by the reaction of oxygen, ammonia and an unsaturated hydrocarbon in a fluid bed reactor having at least two serially connected catalyst-containing zones, with one a catalyst-regenerating zone and the other a dense-phase fluidized bed reaction zone, the method essentially comprising contacting the catalyst in the regeneration zone with oxygen plus between about 3 and about 90 percent of the total amount of ammonia supplied to the reaction. The ammonia may be admixed with the oxygen or fed separately to the catalyst regeneration zone. The remainder of the ammonia is introduced to the reaction zone together with the unsaturated hydrocarbon feed.

Other objects and advantages and specific details of the invention are set forth or rendered obvious by following detailed specification which is to be considered together with the associated drawing which schematically illustrates the preferred form of apparatus for practicing the invention.

It has been discovered that the loss of hydrocarbon feed, e.g., propylene, by conversion to $CO_2$ and $CO$ when oxygen is fed separately to the catalyst regeneration zone as taught by U.S. Pat. No. 3,427,343, is due to the presence of hydrocarbon absorbed on the catalyst particles recycled from other sections of the reactor. Unsaturated hydrocarbons such as propylene, isobutylene, etc., tend to be absorbed by the catalyst but very little, if any, ammonia is absorbed by the catalyst. Accordingly, if oxygen alone is introduced to the regeneration zone as taught by U.S. Pat. No. 3,427,343, it reacts readily with the absorbed hydrocarbon to produce $CO_2$ and $CO$. This undesired oxidation reaction can be minimized by supplying ammonia to the regeneration zone in a quantity sufficient to react with the absorbed hydrocarbon to produce the desired unsaturated nitrile product. Although all of the ammonia normally supplied to the reactor may be fed to the regeneration zone, it is not necessary to do so since the concentration of hydrocarbon in that zone is low. On the other hand, at least about 3 percent of the total ammonia feed is required to be delivered to the regeneration zone to avoid conversion of absorbed hydrocarbon to $CO_2$ and $CO$. Accordingly in practice between about 3 and about 90 percent (and preferably 10 to 30 percent) of the total ammonia feed is delivered to the regeneration zone, with the remainder being introduced to the same reaction zone or zones as the unsaturated hydrocarbon.

Among the unsaturated hydrocarbons which may be used in the practice of this invention are: (A) olefins, e.g., propylene; butene-1; butene-2; isobutylene; pentene-1; pentene-2; 3-methylbutene-1; 2-methyl-butene-2; hexene-1; hexene-2; 4-methyl-pentene-1; 3,3-dimethyl-butene-1; 4 methyl-pentene-2; and octene-1; (B) cyclic unsaturated hydrocarbons, e.g., cyclopentene; cyclohexene; and 3-methyl cyclohexene: and (C) aromatic hydrocarbons such as toluene, xylene, phenylpropene, methylnaphthalene, etc., as well as homologs and analogs thereof, and also mixtures of the same. The preferred reactants are mono-olefins having the structure

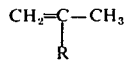

where R is a member selected from the group consisting of hydrogen or a methyl radical, the invention having particular application to the production of acrylonitrile and methacrylonitrile from propylene and isobutylene respectively.

Any source of molecular oxygen may be used. Preferably it is introduced in the form of air for economic reasons. The molar ratio of oxygen to unsaturated hydrocarbon should be in the range of 0:5 : 1 to 3 : 1. For conversion of propylene and isobutylene, best results are achieved with a molar ratio of oxygen to olefin in the range of 1 : 1 to 2 : 1.

U.S. Pat. Nos. 3,427,343 and 3,230,246 disclose that the molar ratio of ammonia to olefin should be between 0.05 : 1 to 5 : 1 (although there is no real upper limit, there is generally no point in exceeding the 5 : 1 ratio). However, these same references also teach that the lower limit should be at least 1 : 1 if formation of oxygenated derivatives of the olefin is to be avoided. Accordingly in industrial practice it is customary to increase the amount of ammonia by at least 10 percent and more often 15–25 percent above that required to maintain the stoichiometric ratio of 1 : 1. This invention does not require more ammonia than has been used heretofore but rather makes it possible to operate closer to the stoichometric ratio of 1 : 1 and still avoid formation of any substantial amount of oxygenated olefin derivatives.

As in prior art processes, water may be used in the reaction mixture (in amounts such as described in said U.S. Pat. Nos. 3,230,246 and 3,427,343) to obtain well-known beneficial effects, but reactions not involving water are also to be considered within the scope of this invention.

Any one of a plurality of well-known ammoxidation catalysts which will function to catalyze the reaction of oxygen, ammonia, and an unsaturated hydrocarbon to produce the corresponding unsaturated nitrile may be used to practice this invention. For example, in converting propylene and isobutylene to acrylonitrile and methacrylonitrile, respectively, the catalyst may consist of the combined oxides of antimony and uranium prepared as described in U.S. Pat. No. 3,427,343. Other usable catalysts are the bismuth, tin, and antimony salts of phosphomolybdic acid and molybdic acid, bismuth silicomolybdate, bismuth silicophosphomolybdate, and bismuth phosphotungstate, as disclosed in U.S. Pat. Nos. 2,904,580, 2,941,007, 3,044,966, 3,050,546, and 2,941,007. Additional preferred catalysts useful in the invention are the combined oxides of antimony and iron, antimony and thorium, antimony and cerium, and antimony and manganese, as well as catalysts of the type disclosed in U.S. Pat. Nos. 2,499,055, 2,828,325, 3,142,697, 3,186,955, 3,312,710, 3,200,081, 3,200,084, 3,248,340, 3,264,225, 3,328,315, 3,341,471 and 3,433,823. Still other catalysts which may be used are described in U.S. Pat. No. 2,481,826, British Pat. Nos. 874,593, 904,418, 1,195,037 and 1,246,108, French Pat. No. 1,278,289, Canadian Pat. No. 619,497, and Belgium Pat. Nos. 592,434, 593,097, 598,511, 603,030, 612,136, 615,605 and 603,031. The catalysts may be prepared by various methods known to those skilled in the art of catalyst preparation. They may be formed as pellets or spheres in accordance with conventional techniques, with the particles consisting solely of the catalyst or of a silica or other support impregnated with the catalyst. Preferably, the catalyst particle size is in the order of 50 to 100 microns (i.e., 100 mesh or finer), but larger or smaller size particles may be used.

The process is conducted at those temperatures and pressures which are typical of processes for conversion of unsaturated hydrocarbons to unsaturated nitriles, the temperature and pressure requirements being determined by the reaction mixture and the desired product. For example, for conversion of propylene and isobutylene to acrylonitrile and methacrylonitrile, respectively, the temperature may be in the range of 500° to 1,000°F, preferably 750°–925°F, and the pressure should be atmospheric or slightly higher, but no more than 3–5 atmospheres. Preferably the pressure should be 5–30 psig.

The optimum contact time will, of course, vary with the unsaturated hydrocarbon being treated. In general the contact time may be in the range of 0.1 to 50 seconds, preferably from 1 to 15 seconds.

While the process may be carried out on an intermittent basis, inn practice it is carried out continuously for economic reasons. The reactor must comprise at least two catalyst-containing zones communicating with each other, the first-in-line being equipped with means for introducing molecular oxygen and ammonia, either separately or admixed, and the other being equipped with means for introducing the hydrocarbon feed (and also that part of the ammonia not introduced to the first-in-line zone). Additionally, the reactor should comprise a catalyst-disengaging zone in which the catalyst is disengaged from the reactor effluent. As an optional feature, the reactor may also include means such as cyclones of filters for recovering fines elutriated from the catalyst bed or beds. The catalyst separating from the reactor effluent is recycled to the first-in-line catalyst-containing zone for regeneration and reaction of catalyst-absorbed hydrocarbon with ammonia and oxygen.

Preferably the invention is practiced using a reactor in which the different catalyst containing zones are in a vertical relationship, with the catalyst regeneration zone to which the oxygen and ammonia are introduced being at the bottom, followed in turn by the dense phase fluidized bed reaction zone and the disengaging zone. If desired, the reactor may comprise more than one dense phase reaction zone or the reaction zone may be subdivided into a plurality of chambers or compartments set apart by a series of spaced foraminous members or perforated trays which may, for example, be flat, conical, or pyramidal screens, gratings, or perforated plates (with the openings therein sized for optimum operation), according to the practice described in U.S. Pat. Nos. 3,230,246 and 2,427,343. Where the reactor comprises a plurality of reaction zones, it is preferred that the hydrocarbon be introduced into a zone which is at least one removed downstream from the catalyst regeneration zone into which oxygen and ammonia are introduced as above described.

For better control of reaction temperature, it may be desirable to include heat exchanger coils or tubes within the reaction zone or zones.

The products of the reaction may be recovered by any of several different methods known to those skilled in the art, preferably by scrubbing the gaseous reactor effluent with cold water or other appropriate solvent. Unreacted hydrocarbon and oxygen recovered from the effluent may be recycled through the reactor.

The invention will be better understood by reference to the drawing which illustrates schematically one form of reactor suitable for carrying out the improved process herein described. In the drawing, a vertical reactor 2 contains at its bottom end a gaseous fluid distributor grid 4 having openings for throughflow of reactant gases and which functions as a catalyst bed support. The reactor may also have a perforated baffle plate 6 extending across its cross-section to facilitate establishing two zones 8 and 10 with a selected catalyst fluidized as described below. Molecular oxygen, preferably in the form of air, is introduced to the bottom of the reactor by a line 12. Ammonia gas is introduced to the bottom of the reactor by a line 14 and to zone 10 by a line 16. Unsaturated hydrocarbon is introduced to zone 10 via a line 18. The oxygen and the ammonia feeds introduced via lines 12 and 14 pass upward through the grid 4 and the baffle 6 at a velocity sufficient to fluidize the catalyst solids withing the zones 8 and 10, i.e., sufficient to maintain the catalyst particles in a turbulent suspension. The fluid catalyst bed in the zone 10 is maintained at a selected height below the top of the reactor so as to provide a disengaging zone 20 in which the catalyst particles are disengaged from the reactor effluent. A cyclone separator 24 is provided in the disengaging zone to separate catalyst fines entrained in the reactor effluent. The cyclone separator is provided with a dip-leg 26 for returning the separated fines back to the regeneration zone. Alternatively the fines separated by the cyclone 24 may be recycled too the zone 10. The effluent is removed from the reactor by means of a line 28 leading to a product recovery unit 30 where the nitrile product is recovered by any of the methods known to those skilled in the art, e.g., by scrubbing with water or other suitable solvent. The unreacted hydrocarbon and any unreacted molecular oxygen may be recycled to the reactor as shown by the borken line 32 leading to zone 10. In the operation of the reactor, catalyst is continuously circulated through the several zones, with the catalyst being continually regenerated in zone 8 by the molecular oxygen and the reaction whereby the hydrocarbon feed is converted to the desired nitrile product occurs continuously in the fluidized bed reaction zone 10. Additionally whatever unsaturated hydrocarbon is absorbed by the recycled catalyst particles is converted to the desired nitrile product in regeneration zone 8 by reaction with the ammonia and oxygen introduced via lines 12 and 14.

The gas velocities should permit a contact time in the range of 0.1 to 50 seconds in each of the zones 8 and 10, and preferably a contact time of 1 to 15 seconds. As used herein the term "contact time" is defined as the length of time in seconds which a unit volume of gas measured under the conditions of reaction is in contact with the unit volume of catalyst.

By way of example, conversion of propylene and isobutylene to acrylonitrile and methacrylonitrile respectively using the apparatus shown in the drawings may be carried out using a catalyst consisting of the combined oxides of antimony and uranium prepared as described in U.S. Pat. No. 3,427,343 and with an average particle size of about 100 microns. The propylene or isobutylene feed, oxygen in the form of air, and ammonia are introduced at rates providing a molar ratio of oxygen to olefin of 1.5 to 1 and a molar ratio of ammonia to olefin of about 1 to 1. About 10 percent of the total ammonia feed is delivered to the regeneration zone and the remainder is delivered to the reaction zone 10. Additionally, water may be introduced to the reaction zone at a rate providing a molar ratio of water to olefin of about 4:1. The reactions are carried out at a temperature in the range of 750°–925° and a pressure of 5–30 psig. The gas velocities are set so as to provide a contact time of about 5 seconds.

It will be appreciated that this same process may be used for producing nitriles other than acrylonitrile and methacrylonitrile, by the ammoxidation of the corresponding hydrocarbon, e.g., 2 - butenenitrile from 2 - butene; 2 - pentenenitrile from 2 - pentene; 2 - methyl - 2 -butenenitrile from 2 - methyl - 2 - butene; 2 - hexenenitrile from 2 - hexene; 2 - methyl - 2 - pentenenitrile from 2 - methyl - 2 - pentene; 3 - methyl - 2 - pentenenitrile from 3 - methyl - 2 - pentene; 1, 4 - cyano [1, 4 - butadiene] from 2, 4 - hexadine; [1, 5 - cyano 1, 4 - pentadiene] from 2, 4 heptadiene; benzonitrile from toluene; tolunitrile; phthalonitrile, and iso- and terephthalonitrile from the xylene isomers; 1 - phenylpropene - nitrile from 1 - phenylpropene; naphthylnitrile from methylnaphthalene; 1, 4 - cyanonaphthalene from 1, 4 - dimethylnaphthalene; 1, 2, 4 - tricyanobenzene and 1, 3, 5 - tricyanobenzene from pseudocumene and mesitylene, respectively; 1, 2, 4, 5 - tetracyanobenzene from durene; and cyanopyridine from picoline or from 2, 5 - lutidine; etc.

Of course the invention may be practiced otherwise than as specifically described and illustrated. Thus the ammonia and air may be admixed prior to entering the bottom end of the reactor or the ammonia supplied to the regeneration zone may be introduced directly to that zone or at a point near to the distribution grid 4, in which case the oxygen feed also may be introduced immediately below the grid 4 so as to assure adequate mixing with the ammonia.

The essential advantages derived from the practice of this invention comprises a reduction in the amount of hydrocarbon feed lost by oxidation to CO and $CO_2$, the ability to achieve superior yield without having to resort to a plurality of serial reactors or reaction zones (although the invention permits the use of serial reactors or reaction zones if desired), ability to operate efficiently with molar ratios of ammonia to hydrocarbon close to or at the stoichiometric ratio of 1 : 1 without formation of any substantial quantity of oxygenated hydrocarbon derivatives, and high average level of catalyst activity.

What is claimed is:

1. A process for producing an unsaturated nitrile by the reaction of an unsaturated hydrocarbon selected from the class consisting of mono-olefinically unsaturated alkenes having at least 3 carbon atoms, and cycloalkenes, alkyl and alkenyl substituted benzenes and naphthalenes with ammonia and oxygen in a reactor containing a fluidized bed of an ammoxidation catalyst characterized by a catalyst regeneration zone and a reaction zone located above the said regeneration zone, said process comprising the steps of introducing all of the unsaturated hydrocarbon supplied to said reaction into said reaction zone, introducing said oxygen into said regeneration zone, introducing between about 3 percent and about 90 percent of the total amount of ammonia supplied to said reaction to said regeneration zone and introducing the remainder of said total amount of ammonia to said reaction zone, maintaining a reaction temperature between about 500° and 1000°F in said reaction zone, and passing said hydrocarbon, ammonia and oxygen upwardly through said reaction zone.

2. The process of claim 1 wherein said oxygen is supplied in the form of air.

3. The process of claim 2 wherein said bed is fluidized by said air.

4. The process of claim 1 further including recovering the effluent product from said reaction at the top of said reactor, separating catalyst fines from said effluent product, and recycling said fines to said regeneration zone.

5. The process of claim 1 wherein 10–30 percent of the total amount of ammonia supplied to said reaction is introduced to said regeneration zone and the remainder is supplied to said reaction zone.

6. The process of claim 1 wherein the molar ratio of total ammonia to total hydrocarbon introduced to said reactor is in the range of about 0.05:1 to 5:1.

7. The process of claim 1 wherein said hydrocarbon is propylene or isobutylene and the product of said reaction is acrylonitrile or methacrylonitrile respectively.

8. The process of claim 1 wherein said reaction zone comprises a series of communicating compartments with each compartment containing said fluidized catalyst.

9. A process for producing an unsaturated nitrile by the reaction of an unsaturated olefin with ammonia and oxygen in a reactor containing a fluidized bed of an ammoxidation catalyst characterized by a catalyst regeneration zone and a reaction zone located above the said regeneration zone, said olefin being a mono-olefin having the structure

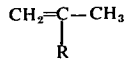

where R is hydrogen or methyl, said process comprising the steps of introducing all of said unsaturated olefin into said reaction zone, introducing all of said oxygen into said regeneration zone, introducing between 3 and about 90 percent of the total amount of ammonia supplied to said reaction to said regeneration zone and introducing the remainder of said total amount of ammonia to said reaction zone, maintaining a reaction temperature between about 500° and 1000°F in said reaction zone, and passing said olefin, ammonia and oxygen upwardly through said reaction zone for reaction in the presence of said catalyst.

10. A process according to claim 9 wherein said olefin is propylene and said unsaturated nitrile is a acrylonitrile.

11. A process according to claim 9 wherein said olefin is propylene and said unsaturated nitrile is methacrylonitrile.

12. In a process for producing an unsaturated nitrile by reacting a mono-olefinically unsaturated olefin with ammonia and oxygen in a reactor containing a fluidized bed of an ammoxidation catalyst characterized by a catalyst regeneration zone and a reaction zone maintained at a temperature between about 500° and 1000°F located above said regeneration zone, said olefin being propylene or isobutylene, said oxygen being introduced to said regeneration zone and said olefin being introduced only to said regeneration zone, the improvement comprising introducing about 3 to about 90 percent of the total amount of ammonia supplied to said reaction to said regeneration zone and introducing the remainder of said total amount of ammonia to said reaction zone.

13. The process of claim 1 wherein said unsaturated hydrocarbon comprises a mono-olefinically unsaturated alkene selected from the group consisting of propylene, butene-I, butene-2, isobutylene, pentene-I, pentene-2, 3-methyl-butene-I, 2-methybutene-2, hexene-I, hexene-2, 4-methyl-pentene-I, 3,3-dimethylbutene-I, 4 methyl-pentene-2, and octene-I; a cyclic unsaturated hydrocarbon selected from the group consisting of cyclopentene, cyclohexene, and 3-methyl cyclohexene; and an aromatic hydrocarbon selected from the group consisting of toluene, xylene, phenylpropene and methylnaphthalene.

14. The process of claim 12 wherein said mono-olefinically unsaturated olefin is selected from the group consisting of propylene, butene-I, butene-2; isobutylene, pentene-I, pentene-2, 3-methyl-butene-I, 2-methyl-butene-2, hexene-I, hexene-2, 4-methyl-pentene-I, 3,3-dimethyl-butene-I, 4 methyl-pentene-2, and octene-I.

* * * * *